United States Patent
Chen et al.

(10) Patent No.: US 9,454,566 B2
(45) Date of Patent: Sep. 27, 2016

(54) DEVICE FOR DATA MANAGEMENT

(71) Applicant: Mackay Memorial Hospital, Taipei (TW)

(72) Inventors: Chi-Kuan Chen, Taichung (TW); Yen-Ta Lu, Taipei (TW); Wan-Ting Chen, New Taipei (TW)

(73) Assignee: Mackay Memorial Hospital, Taipei (TW)

( * ) Notice: Subject to any disclaimer, the term of this patent is extended or adjusted under 35 U.S.C. 154(b) by 540 days.

(21) Appl. No.: 13/939,764

(22) Filed: Jul. 11, 2013

(65) Prior Publication Data

US 2014/0019469 A1 Jan. 16, 2014

(30) Foreign Application Priority Data

Jul. 11, 2012 (TW) .............................. 101124850 A

(51) Int. Cl.
*G06F 17/30* (2006.01)
*G06F 19/00* (2011.01)

(52) U.S. Cl.
CPC ....... *G06F 17/30386* (2013.01); *G06F 19/322* (2013.01)

(58) Field of Classification Search
USPC ......................................... 707/754, 758, 803
See application file for complete search history.

(56) References Cited

U.S. PATENT DOCUMENTS

| | | | | |
|---|---|---|---|---|
| 6,070,141 A * | 5/2000 | Houvener | ............ | G06Q 20/04 235/380 |
| 8,205,264 B1 * | 6/2012 | Kailash | .............. | H04L 67/02 709/223 |
| 8,295,179 B2 * | 10/2012 | Comeras | ............ | H04L 43/0894 370/229 |
| 8,316,237 B1 * | 11/2012 | Felsher | ................ | H04L 9/0825 380/282 |
| 8,542,117 B1 * | 9/2013 | Miasnik | ................ | G08B 23/00 340/540 |
| 8,762,288 B2 * | 6/2014 | Dill | ........................ | G06Q 30/02 705/16 |
| 8,937,548 B1 * | 1/2015 | Miasnik | ................ | G08B 23/00 340/540 |
| 8,983,998 B1 * | 3/2015 | Spence | ............... | G06F 17/3087 707/749 |
| 9,044,675 B2 * | 6/2015 | Stafford | .................. | A63F 13/79 |
| 9,189,788 B1 * | 11/2015 | Robinson | ......... | G06Q 20/40145 |
| 9,223,897 B1 * | 12/2015 | Gross | ................ | G06F 17/30941 |
| 2002/0103801 A1 * | 8/2002 | Lyons | ..................... | G06Q 30/02 |
| 2002/0199194 A1 * | 12/2002 | Ali | ........................ | G11B 27/105 725/46 |
| 2005/0022234 A1 * | 1/2005 | Strothman | ......... | H04N 5/44543 725/34 |
| 2008/0288494 A1 * | 11/2008 | Brogger | ................ | G06Q 30/02 |
| 2009/0070301 A1 * | 3/2009 | McLean | ............. | G06F 17/3061 |
| 2009/0210444 A1 * | 8/2009 | Bailey | .................... | G06Q 30/02 |

(Continued)

*Primary Examiner* — Hanh Thai
(74) *Attorney, Agent, or Firm* — Womble Carlyle Sandridge & Rice LLP

(57) ABSTRACT

A device for data management, the device is in communication with a memory and includes: a verification module configured to receive a first identity information and a first request and verify the first identity information; a search module configured to search for at least one first data stored in the memory in response to the first request if the first identity information is verified, the at least one first data being assigned a first rating point; and an evaluation module configured to receive a second rating point associated with the first identification information, retrieve the first rating point from the at least one first data and generate a third rating point in accordance with the verified first identity information, the first rating point and the second rating point and store the third rating point in the memory.

21 Claims, 4 Drawing Sheets

(56) References Cited

U.S. PATENT DOCUMENTS

| | | | |
|---|---|---|---|
| 2010/0030764 A1* | 2/2010 | Koren | G06Q 30/0201 705/7.29 |
| 2010/0058183 A1* | 3/2010 | Hamilton, II | G06Q 30/02 715/706 |
| 2011/0004504 A1* | 1/2011 | Ives | G06Q 30/02 705/7.29 |
| 2012/0084818 A1* | 4/2012 | Ali | G11B 27/105 725/46 |
| 2012/0163221 A1* | 6/2012 | Miyazawa | H04L 43/0882 370/252 |
| 2015/0097672 A1* | 4/2015 | Miasnik | G08B 27/00 340/540 |

* cited by examiner

DEVICE FOR DATA MANAGEMENT

CROSS-REFERENCE TO RELATED APPLICATION(S)

The present application claims priority to Taiwanese Patent Application No. 101124850, filed on Jul. 11, 2012, the content of which is incorporated herein by reference in its entirety.

BACKGROUND

The present disclosure relates generally to data management. More particularly, the present disclosure relates to a device for data management.

Myriads of information/data now are able to be transferred at a high speed thanks to the Internet. More and more users are willing to pay for the data of interest or offer something other than money in exchange of the desired data. On the other hand, data providers are also encouraged to upload or provide more data to an accessible server or database. However, various factors could be involved in determining the value of the provided data. Accordingly, it is desired to have a reasonable evaluation scheme so that both data providers and users may be satisfied with the data transaction. Moreover, it is also desired to have data management device and method to facilitate data transaction.

BRIEF SUMMARY OF THE INVENTION

Example embodiments of the present disclosure may provide a device for data management, the device which is in communication with a memory includes: a verification module configured to receive a first identity information and a first request and verify the first identity information; a search module configured to search for at least one first data stored in the memory in response to the first request if the first identity information is verified, the at least one first data being assigned a first rating point; and an evaluation module configured to receive a second rating point associated with the first identification information, retrieve the first rating point from the at least one first data and generate a third rating point in accordance with the verified first identity information, the first rating point and the second rating point and store the third rating point in the memory.

Some example embodiments of the present disclosure may also provide a device for data management, the device which is in communication with a memory includes: a verification module configured to receive a first identity information and a first request and verify the first identity information; a search module configured to search for at least one first data stored in the memory in response to the first request if the first identity information is verified; and an evaluation module configured to generate a first code and a second code, both the first and second codes are associated with the first identification information, wherein the first code represents a published document does exist and the second code represents whether the at least one first data is cited in the published document and the evaluation module is configured to further generate a first rating point in accordance with the first and second codes and store the first rating point in the memory.

Some example embodiments of the present disclosure may provide a device for data management, the device which is in communication with a memory includes: a verification module configured to receive a first identity information and a first request and verify the first identity information and the first request; a search module configured to search for at least one first data stored in the memory in response to the first request if the first identity information and the first request are verified, the at least one first data is assigned a first rating point; an evaluation module configured to receive a second rating point associated with the first identification information, retrieve the first rating point from the at least one first data and generate a third rating point in accordance with the verified first identity information, the first rating point and the second rating point and store the third rating point in the memory, the evaluation module is configured to further generate a first code and a second code, both the first and second codes are associated with the first identification information, wherein the first code represents a published document does exist and the second code represents whether the at least one first data is cited in the published document, the evaluation module is configured to generate a fourth rating point in accordance with the first and second codes and store the fourth rating point in the memory and the evaluation module is configured to generate a fifth rating point in accordance with the third rating point and the fourth rating point and store the fifth rating point in the memory; and a determination module configured to retrieve the third, fourth or fifth rating point in the memory to determine the classification of the first identity information.

Additional features and advantages of the present invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

In the drawings.

DETAILED DESCRIPTION OF THE INVENTION

Reference will now be made in detail to the present examples of the invention, examples of which are illustrated in the accompanying drawings. Wherever possible, the same reference numbers will be used throughout the drawings to refer to the same or like parts.

Figure 1:
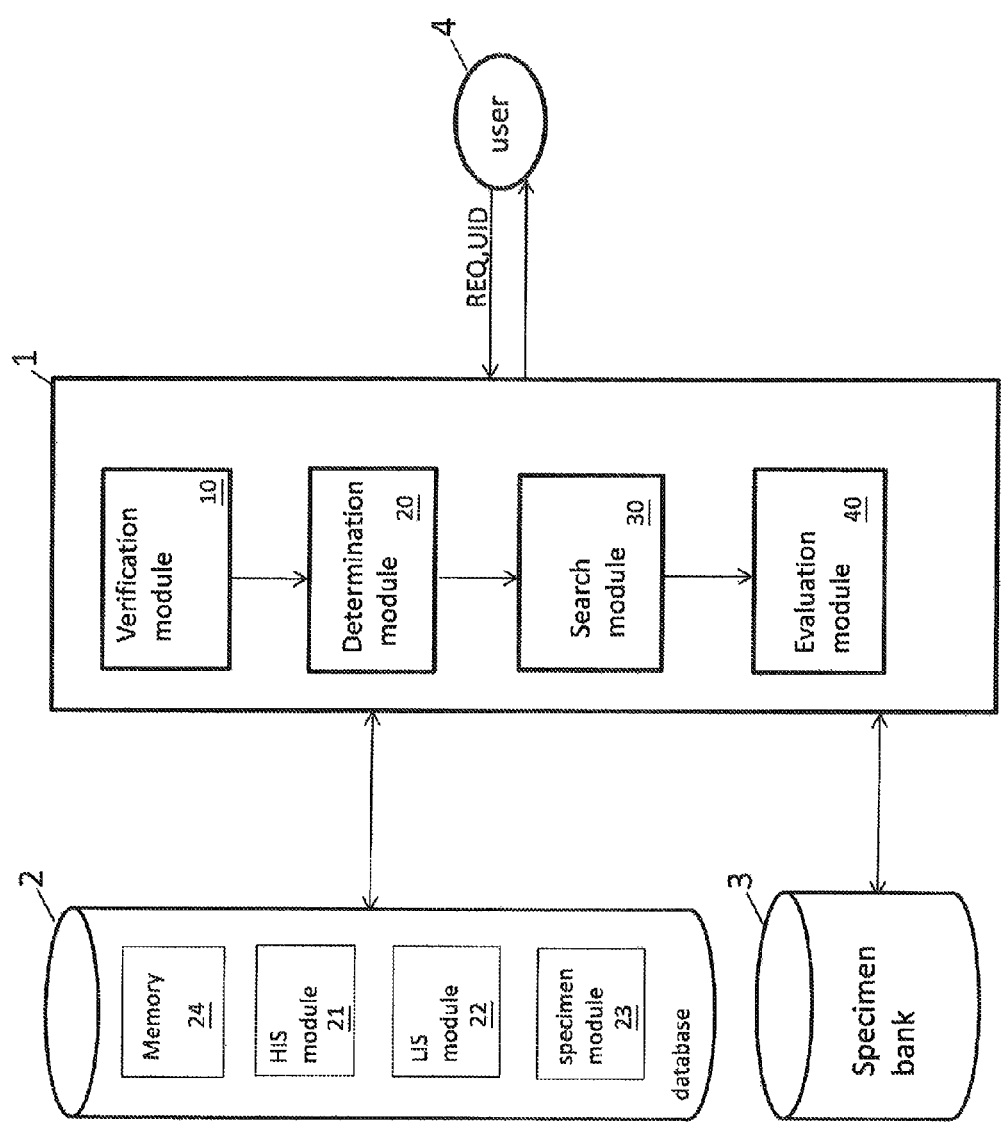
FIG. 1 is a block diagram of a computing device 1 in accordance with an example embodiment of the present disclosure.

FIG. 1 is a block diagram of a computing device 1 in accordance with an example embodiment of the present disclosure. Referring to FIG. 1, the computing device 1 may be coupled to a database 2. In one example embodiment, the computing device 1 may include but is not limited to a server, a processor, a desktop, a laptop, a tablet computer, an integrated processing circuit or the like. In one example embodiment, the database 2 may include but is not limited to a hospital information system (HIS) module 21, a library information system (LIS) module 22 and a specimen module 23. The HIS module 21 may at least contain patients' medical records, which include patients' profile such as age, height, weight or the like. Furthermore, the LIS module 22 may at least contain patients' test results such as X-ray images, computer tomography (CT) images, ultrasonic images, magnetic resonant images (MRI) endoscope images, skin images, microscopic images or the like. Moreover, the specimen module 23 may at least contain data associated with physical specimens/samples collected from patients' bodies and stored in a specimen bank 3. A user 4 may access the database 2 through the computing device 1. Furthermore, the user 4 may also obtain the desired specimen(s) from the specimen bank 3 in accordance with the associated data in the specimen module 23.

More particularly, the computing device 1 may include but is not limited to a verification module 10, a determination module 20, a search module 30 and an evaluation module 40. The user 4 may provide the computing device 1 with a user identification (UID) and a request (REQ). In one example embodiment, the UID may include but is not limited to a set of account name and password. The verification module 10 may be configured to verify the UID. If the UID is verified, the user 4 may access the database 2 through the computing device 1.

In another example embodiment, in addition to the UID, the verification module 10 may further verify the REQ in accordance with a set of rules predetermined by for example an institutional review board (IRB) and stored in a memory 24 of the database 2. The database 2 can only be accessed by the user 4 when UID and REQ are both verified by the verification module 10.

In one example embodiment, the REQ which may at least contain keyword(s) related to the data of interest. For example, the user 4 may want to obtain lung cancer-related data for research and the REQ may contain the keywords of "lung cancer." Once the UID or the UID and REQ are verified, the REQ may then be sent to the search module 30. The search module 30 may search for the data of interest in the database 2 in response to the REQ. Details of the operation of the search module 30 will be discussed in the example embodiment below with reference to FIG. 2.

Figure 2:
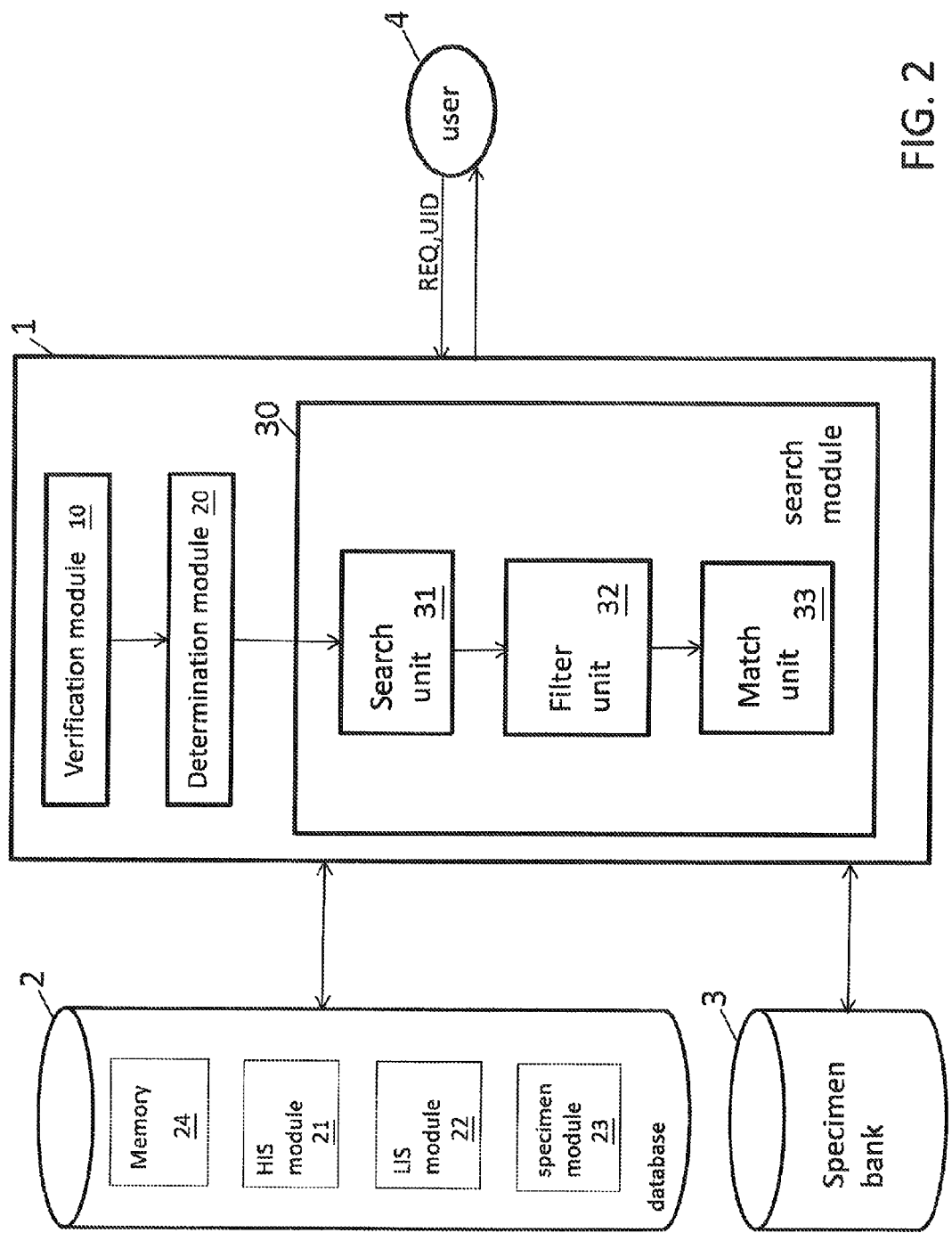
FIG. 2 is a block diagram of a computing device 1 in accordance with another example embodiment of the present disclosure.

FIG. 2 is a block diagram of a computing device 1 in accordance with another example embodiment of the present disclosure. Referring to FIG. 2, the search module 30 may include but is not limited to a search unit 31, a filter unit 32 and a match unit 33. The search unit 31 may at least be configured to search for the data of interest in the database 2 in response to the REQ. In one example embodiment, the search results may contain patients' personal information that cannot be revealed, for example, a patient's name, identification number, passport number, education background, contact information, phone number, race, color of skin, kinship, appearances or the like. Therefore, the search results may then be transmitted to the filter unit 32, which may at least be configured to remove the personal information from the search results and send the filtered search results to the user 4.

Furthermore, the user 4 may also want to obtain physical specimens/samples (such as tissue specimens or cell specimens) collected from the patients in the hit list of the search results, if any. The specimens of interest may be obtained with the help of the match unit 33, which will be discussed in the following example embodiment with reference to FIGS. 3A and 3B.

Figure 3A:
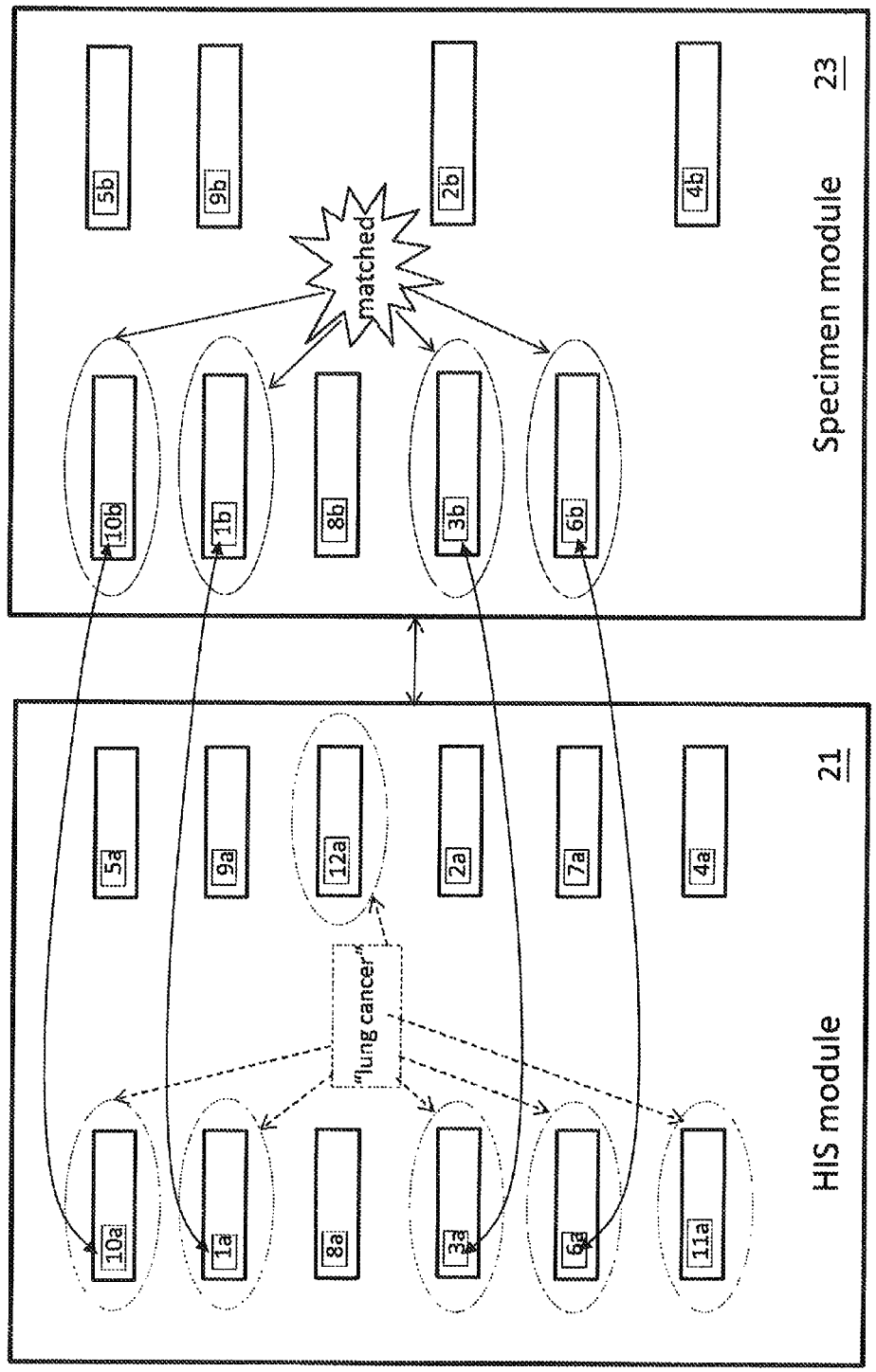
FIGS. 3A and 3B illustrate a search process for the specimens of interest in accordance with an example embodiment of the present disclosure.
Figure 3B:
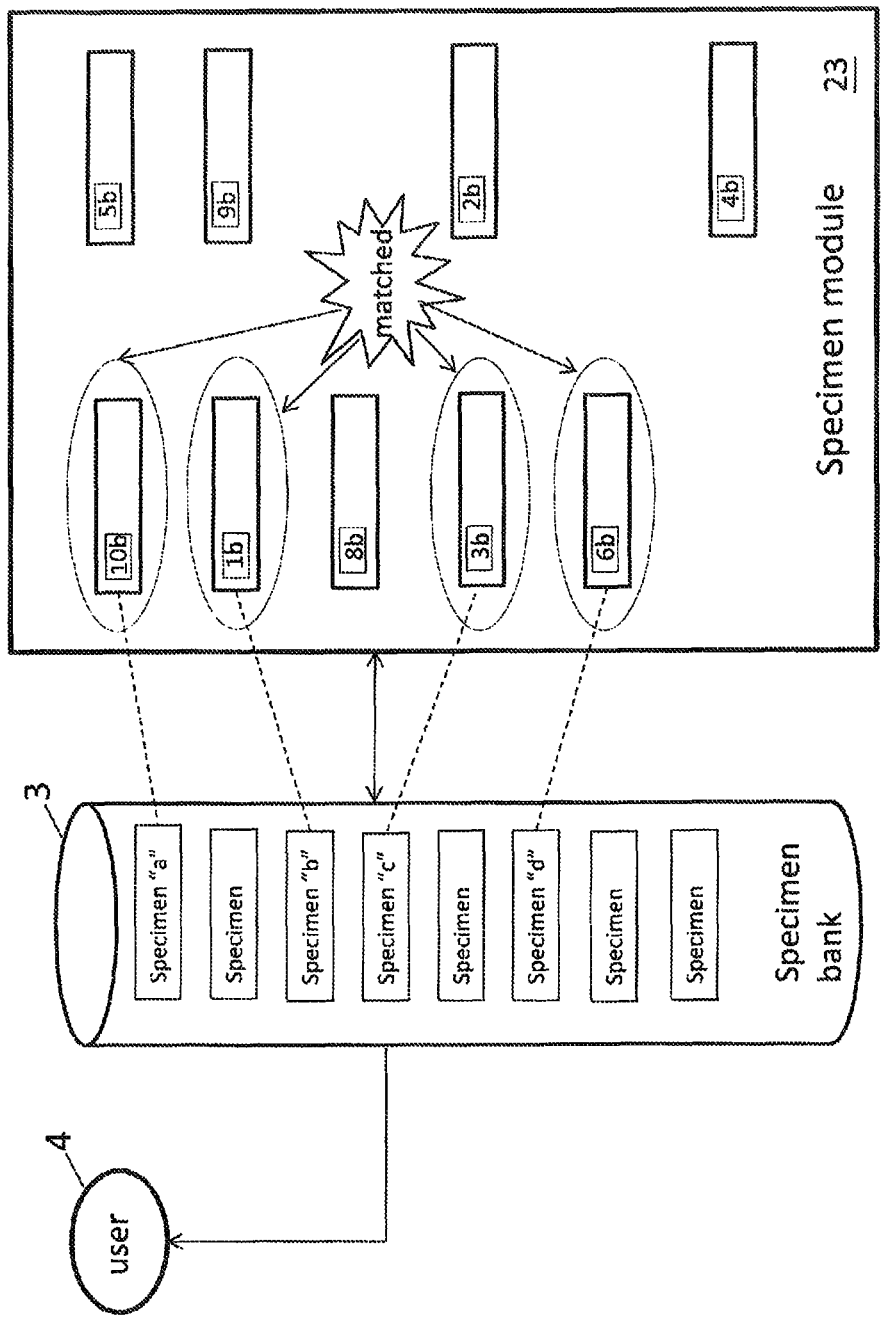

FIGS. 3A and 3B illustrate a search process for the specimens of interest in accordance with an example embodiment of the present disclosure. Referring to FIG. 3A, each the data stored in the specimen module 23 may be assigned a unique identifier, such as an index number. As shown in FIG. 3A, each data in the specimen module 23 may be assigned an index number as follows "10b," "1b," "8b," "3b," "6b," "5b," "9b," "2b" and "4b."

Each the medical record stored in the HIS module 21 may also be assigned an identifier relative to the unique identifier assigned to each corresponding data stored in the specimen module 23. In this example embodiment, each the medical record stored in the HIS module 21 may be assigned an index number as follows "10a," "1a," "8a," "3a," "6a," "11a," "5a," "9a," "12a," "2a," "7a" and "4a," wherein the medical records with index numbers of "10a," "1a," "3a," "6a," "11a" and "12a" may be related to lung cancer. The match unit 33 may match a medical record stored in the HIS module 21 with the corresponding data stored in the specimen module 23 in accordance with the assigned identifiers or index numbers. In this example embodiment, each the index number "10b," "1b," "3b" and "6b" may be relative to each index number "10a," "1a," "3a" and "6a." Accordingly, the match unit 33 may find the match result, e.g. matched identifiers, and retrieve the four unique identifiers "10b," "1b," "3b" and "6b" from the match result and send the retrieved unique identifiers "10b," "1b," "3b" and "6b" to the specimen bank 3. An identifier may be randomly assigned to each medical record and data such that the user 4 cannot trace the personal information.

Referring to FIG. 3B, each the specimen stored in the specimen bank 3 may also be assigned an identifier relative to the unique identifier assigned to each corresponding data stored in the specimen module 23. The management system of the specimen bank 3 may receive the unique identifiers "10b," "1b," "3b" and "6b" from the match unit 33. The management system of the specimen bank 3 may further use the received unique identifiers to identify specimens with assigned identifiers "a," "b," "c" and "d," which correspond to the unique identifiers "10b," "1b," "3b" and "6b". The management system of the specimen bank 3 may then deliver the physical specimens "a," "b," "c" and "d" to the user 4. After the data (and specimens, if any) of interest are searched by the computing device 1 and then obtained by the user 4, evaluation process may be performed as will be discussed in the following example embodiment.

Each the data in the database 2 may be assigned a rating point "C1." In one example embodiment, the rating point "C1" may be given by the times the medical records being accessed or downloaded. For example, a medical review module (not shown) resided in the computing device 1 may give a relatively high rating point "5" to a medical record which is accessed or downloaded seven times, and give a relatively low rating point "2" to another medical record which is accessed or downloaded three times. In another example embodiment, the rating point "C1" may reflect the quality of each the data. For example, personnel in charge of medical records review may give a relatively high rating point "5" to a medical record having relatively good quality and give a relatively low rating point "1" to another medical record having relatively bad quality.

The evaluation module 40 may receive a rating point "C2" given to the located data (in response to the REQ) by the user 4. In one example embodiment, the user 4 may appreciate the located medical record and give the medical record a relatively high rating point "5." In another example, the user 4 may find the located medical record not quite useful and give the medical record a relatively low rating point "1."

The evaluation module 40 may generate a rating point "C3" in accordance with the "UID," the rating points "C1" and "C2." In one example embodiment, the rating point "C3" may be determined by the compliance between the rating points "C1" and "C2." Accordingly, if both "C1" and "C2" are relatively high (or low), which means "C1" is in compliance with "C2," the evaluation module 40 may generate a relatively high rating point "C3." On the other hand, if both "C1" is relatively high (or low) and "C2" is relatively low (or high), which means "C1" is not in compliance with "C2," the evaluation module 40 may generate a relatively low rating point "C3."

The user 4 may use the received medical record(s) from the computing device 1 in his/her research such as thesis/theses, paper(s), patent(s) or the like. In one example embodiment, still referring to FIG. 1, the evaluation module 40 may generate a code "PUB" associated with the "UID" if being notified of the publication of the user 4's research. If any medical record(s) ever being used by the user 4 is/are cited in his/her published research, the evaluation module 40 may generate a code "CIT" associated with the "UID." If the user 4 does access the medical record(s) but none of them is found in his/her published research, the evaluation module 40 may generate a code "NCIT" associated with the "UID." The evaluation module 40 may further generate a rating point "C4" in accordance with the user 4's "UID," the codes "PUB" and "CIT/NCIT." In one example embodiment, the rating point "C4" may be relatively high if the code "CIT" is used to generate the rating point "C4," and the rating point "C4" may be relatively low if the code "NCIT" is used to generate the rating point "C4."

In one example embodiment, the code "PUB" may also contain information in relation to user 4's published research, for example, if the user's research is published in "Nature," the code "PUB" may include the concerning description. In another example embodiment, the code "PUB" may contain the classification of published documents, for example, the more prestigious the published document is, the higher raking it may get. Accordingly, the evaluation module 40 may determine the rating point "C4" in accordance with the code "PUB."

In one example embodiment, the evaluation module 40 may generate a rating point "C5" by the following equation:

$$C5=\alpha C3+(1-\alpha)C4 \qquad \text{e.q. (1)}$$

where the factor $\alpha$ is a weight that may be adjust to determine the rating point "C5." The factor $\alpha$ may range from zero to one. In one example embodiment, the factor $\alpha$ may be 0.5 and the rating points "C3" and "C4" thus have same weight, such relation may explain that the rating point "C5" may reflect the feedback of the located data used by the user 4 and the compliance between the rating points "C1" and "C2." In another example embodiment, the factor $\alpha$ may be zero and the rating point "C5" is equivalent to "C4," such relation may explain that the rating point "C5" may reflect the feedback of the located data used by the user 4. In still another example embodiment, the factor $\alpha$ may be one and the rating point "C5" is equivalent to "C3," such relation may explain that the rating point "C5" may reflect the compliance between the rating points "C1" and "C2."

Referring back to FIG. 1, the rating point "C5" may be stored in the memory 24. As the user 4 again uses the "UID" to access the database 2, the rating point "C5" associated with the "UID" may be retrieved from the memory 24 by the determination module 20. Based on the retrieved the rating point "C5," the determination module 20 may be configured to determine the classification of the UID. The data to be accessed by the user 4 may then be determined by the classification of the UID.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

Further, in describing representative examples of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. A device for data management, the device being in communication with a memory and comprising:
    a verification module configured to receive a first identity information and a first request and verify the first identity information;
    a search module configured to search for at least one first data stored in the memory in response to the first request if the first identity information is verified, the at least one first data being assigned a first rating point; and
    an evaluation module configured to receive a second rating point associated with the first identification information, retrieve the first rating point from the at least one first data and generate a third rating point in accordance with the verified first identity information, the first rating point and the second rating point and store the third rating point in the memory,
    wherein the third rating point is determined in accordance with compliance between the first rating point and the second rating point.

2. The device of claim 1, wherein the first rating point increases as the access times of the at least one first data increases.

3. The device of claim 1, wherein the first rating point is determined by the quality of the at least one first data.

4. The device of claim 1, wherein the evaluation module is configured to further generate a first code and a second code, both the first and second codes are associated with the first identification information, wherein the first code represents a published document does exist and the second code represents whether the at least one first data is cited in the published document.

5. The device of claim 4, wherein the first code further represents the classification of the published document.

6. The device of claim 4, wherein the evaluation module is configured to generate a fourth rating point in accordance with the first and second codes.

7. The device of claim 6, wherein the evaluation module is configured to generate a fifth rating point in accordance with the verified first identity information, the first rating point, the second rating point and the fourth rating point and store the fifth rating point in the memory.

8. The device of claim 7 further comprising a determination module configured to retrieve the third or fifth rating point in the memory to determine the classification of the first identity information.

9. The device of claim 1, wherein the verification module further verifies the first request.

10. A device for data management, the device being in communication with a memory and comprising:
   a verification module configured to receive a first identity information and a first request and verify the first identity information;
   a search module configured to search for at least one first data stored in the memory in response to the first request if the first identity information is verified; and
   an evaluation module configured to generate a first code and a second code, both the first and second codes are associated with the first identification information, wherein the first code represents a published document does exist and the second code represents whether the at least one first data is cited in the published document and the evaluation module being configure to further generate a first rating point in accordance with the first and second codes and store the first rating point in the memory,
   wherein the at least one first data is assigned a second rating point and the evaluation module receives a third rating point associated with the first identification information and retrieve the second rating point from the at least one first data, wherein the evaluation module generates a fourth rating point in accordance with the verified first identity information, the second rating point and the third rating point and store the fourth rating point in the memory,
   wherein the fourth rating point is determined in accordance with compliance between the second rating point and the third rating point.

11. The device of claim 10, wherein the first code further represents the classification of the published document.

12. The device of claim 10, wherein the evaluation module generates a fifth rating point in accordance with the first rating point and the fourth rating point and store the fifth rating point in the memory.

13. The device of claim 12 further comprising a determination module configured to retrieve the first, fourth or fifth rating point in the memory to determine the classification of the first identity information.

14. The device of claim 10, wherein the second rating point increases as the access times of the at least one first data increases.

15. The device of claim 10, wherein the second rating point is determined by the quality of the at least one first data.

16. The device of claim 10 further comprising a filter module configured to remove personal information from the at least one first data.

17. The device of claim 10, wherein the verification module further verifies the first request.

18. A device for data management, the device being in communication with a memory and comprising:
   a verification module configured to receive a first identity information and a first request and verify the first identity information and the first request;
   a search module configured to search for at least one first data stored in the memory in response to the first request if the first identity information and the first request are verified, the at least one first data being assigned a first rating point;
   an evaluation module configured to receive a second rating point associated with the first identification information, retrieve the first rating point from the at least one first data and generate a third rating point in accordance with the verified first identity information, the first rating point and the second rating point and store the third rating point in the memory, the evaluation module being configured to further generate a first code and a second code, both the first and second codes are associated with the first identification information, wherein the first code represents a published document does exist and the second code represents whether the at least one first data is cited in the published document, the evaluation module being configured to generate a fourth rating point in accordance with the first and second codes and store the fourth rating point in the memory and the evaluation module being configured to generate a fifth rating point in accordance with the third rating point and the fourth rating point and store the fifth rating point in the memory; and
   a determination module configured to retrieve the third, fourth or fifth rating point in the memory to determine the classification of the first identity information,
   wherein the third rating point is determined in accordance with compliance between the first rating point and the second rating point.

19. The device of claim 18, wherein the first rating point increases as the access times of the at least one first data increases.

20. The device of claim 18, wherein the first rating point is determined by the quality of the at least one first data.

21. The device of claim 18, wherein the first code further represents the classification of the published document.

* * * * *